(12) United States Patent
Edwards

(10) Patent No.: US 8,092,381 B2
(45) Date of Patent: Jan. 10, 2012

(54) THRESHOLD TRAINING SYSTEM

(75) Inventor: Sally Edwards, Sacramento, CA (US)

(73) Assignee: Heart Zones USA, Sacramento, CA (US)

( * ) Notice: Subject to any disclaimer, the term of this patent is extended or adjusted under 35 U.S.C. 154(b) by 716 days.

(21) Appl. No.: 11/809,706

(22) Filed: May 31, 2007

(65) Prior Publication Data

US 2008/0300498 A1    Dec. 4, 2008

(51) Int. Cl.
*A61B 5/00* (2006.01)
(52) U.S. Cl. .................................. 600/300; 128/898
(58) Field of Classification Search .......... 600/508–521, 600/300, 301; 128/898
See application file for complete search history.

(56) References Cited

U.S. PATENT DOCUMENTS

| | | | |
|---|---|---|---|
| 5,308,300 A * | 5/1994 | Chino et al. ................ | 482/52 |
| 5,769,755 A | 6/1998 | Henry et al. | |
| 6,163,718 A | 12/2000 | Fabrizio | |
| 6,174,289 B1 * | 1/2001 | Binder ...................... | 600/532 |
| 6,411,850 B1 | 6/2002 | Kay et al. | |
| 7,151,959 B2 | 12/2006 | Dardik et al. | |
| 2007/0135723 A1 * | 6/2007 | Wang ....................... | 600/520 |

OTHER PUBLICATIONS

Leibetseder et al. "A simple running test to estimate cardiorespiratory fitness" Journal of EXercise Physiology online vol. 5 No. 3, Aug. 2002.*

* cited by examiner

*Primary Examiner* — Scott Getzow
(74) *Attorney, Agent, or Firm* — Temmerman Law Office; Mathew J. Temmerman

(57) ABSTRACT

A system for increasing the fitness level of a fitness enthusiast. The system includes a personalized set of intensity zones corresponding to increasing levels of exercise intensity. The personalization of the system is accomplished through determining a threshold level based on oxygen consumption or a numerical rating of perception of effort or lactate or metabolism that is unique to each individual. From this determination, an anchor point is created upon which the heart rate values for each of eight zones is based. Each zone corresponds to a multiplier that when factored in to the amount time spent in each zone by the individual, yields a total training load value.

15 Claims, 4 Drawing Sheets

| Number | Name | % | Beats Per Minute | | | | | | | | | | | | | | | | |
|---|---|---|---|---|---|---|---|---|---|---|---|---|---|---|---|---|---|---|---|
| Zone 5 c | Red Line C | 110% ↑ | 132 | 138 | 143 | 149 | 154 | 160 | 165 | 171 | 176 | 182 | 187 | 193 | 198 | 204 | 209 | 215 | 220 |
| Zone 5 b | Red Line B | 110% ↕ 105% | 132 ↕ 126 | 138 ↕ 131 | 143 ↕ 137 | 149 ↕ 142 | 154 ↕ 147 | 160 ↕ 152 | 165 ↕ 158 | 171 ↕ 63 | 176 ↕ 168 | 182 ↕ 173 | 187 ↕ 178 | 193 ↕ 184 | 198 ↕ 189 | 204 ↕ 194 | 209 ↕ 200 | 215 ↕ 205 | 220 ↕ 210 |
| Zone 5 a | Red Line A | 105% ↕ 100% | 126 ↕ 120 | 131 ↕ 125 | 137 ↕ 130 | 142 ↕ 135 | 147 ↕ 140 | 152 ↕ 145 | 158 ↕ 150 | 163 ↕ 155 | 168 ↕ 160 | 173 ↕ 165 | 178 ↕ 170 | 184 ↕ 175 | 189 ↕ 180 | 194 ↕ 185 | 200 ↕ 190 | 205 ↕ 195 | 210 ↕ 200 |
| Threshold | Anchor Point | 100% | 120 | 125 | 130 | 135 | 140 | 145 | 150 | 155 | 160 | 165 | 170 | 175 | 180 | 185 | 190 | 195 | 200 |
| Zone 4 | Orange | 100% ↕ 90% | 120 ↕ 08 | 125 ↕ 113 | 130 ↕ 117 | 135 ↕ 122 | 140 ↕ 126 | 145 ↕ 130 | 150 ↕ 135 | 155 ↕ 140 | 160 ↕ 144 | 165 ↕ 149 | 170 ↕ 153 | 175 ↕ 158 | 180 ↕ 162 | 185 ↕ 167 | 190 ↕ 171 | 195 ↕ 176 | 200 ↕ 180 |
| Zone 3 | Yellow | 90% ↕ 80% | 108 ↕ 96 | 113 ↕ 100 | 117 ↕ 104 | 122 ↕ 108 | 126 ↕ 112 | 130 ↕ 116 | 135 ↕ 120 | 140 ↕ 124 | 144 ↕ 128 | 149 ↕ 132 | 153 ↕ 136 | 158 ↕ 140 | 162 ↕ 144 | 167 ↕ 148 | 171 ↕ 152 | 176 ↕ 156 | 180 ↕ 160 |
| Zone 2 | Green | 80% ↕ 70% | 96 ↕ 84 | 100 ↕ 88 | 104 ↕ 91 | 108 ↕ 95 | 112 ↕ 98 | 116 ↕ 102 | 120 ↕ 105 | 124 ↕ 109 | 128 ↕ 112 | 132 ↕ 115 | 136 ↕ 119 | 140 ↕ 123 | 144 ↕ 126 | 148 ↕ 130 | 152 ↕ 133 | 156 ↕ 137 | 160 ↕ 140 |
| Zone 1 | Blue | 70% ↕ 60% | 84 ↕ 72 | 88 ↕ 75 | 91 ↕ 78 | 95 ↕ 81 | 98 ↕ 84 | 102 ↕ 87 | 105 ↕ 90 | 109 ↕ 93 | 112 ↕ 96 | 115 ↕ 99 | 119 ↕ 102 | 123 ↕ 105 | 126 ↕ 108 | 130 ↕ 111 | 133 ↕ 114 | 137 ↕ 117 | 140 ↕ 120 |

| Number | Name | % | Beats Per Minute | | | | | | | | | | | | | | | |
|---|---|---|---|---|---|---|---|---|---|---|---|---|---|---|---|---|---|---|
| Zone 5 c | Red Line C | ← 110% | ← 132 | ← 138 | ← 143 | ← 149 | ← 154 | ← 160 | ← 165 | ← 171 | ← 176 | ← 182 | ← 187 | ← 193 | ← 198 | ← 204 | ← 209 | ← 215 | ← 220 |
| Zone 5 b | Red Line B | 110% ↔ 105% | 132 ↔ 126 | 138 ↔ 131 | 143 ↔ 137 | 149 ↔ 142 | 154 ↔ 147 | 160 ↔ 152 | 165 ↔ 158 | 171 ↔ 63 | 176 ↔ 168 | 182 ↔ 173 | 187 ↔ 178 | 193 ↔ 184 | 198 ↔ 189 | 204 ↔ 194 | 209 ↔ 200 | 215 ↔ 205 | 220 ↔ 210 |
| Zone 5 a | Red Line A | 105% ↔ 100% | 126 ↔ 120 | 131 ↔ 125 | 137 ↔ 130 | 142 ↔ 135 | 147 ↔ 140 | 152 ↔ 145 | 158 ↔ 150 | 163 ↔ 155 | 168 ↔ 160 | 173 ↔ 165 | 178 ↔ 170 | 184 ↔ 175 | 189 ↔ 180 | 194 ↔ 185 | 200 ↔ 190 | 205 ↔ 195 | 210 ↔ 200 |
| Threshold | Anchor Point | 100% | 120 | 125 | 130 | 135 | 140 | 145 | 150 | 155 | 160 | 165 | 170 | 175 | 180 | 185 | 190 | 195 | 200 |
| Zone 4 | Orange | 100% ↔ 90% | 120 ↔ 08 | 125 ↔ 113 | 130 ↔ 117 | 135 ↔ 122 | 140 ↔ 126 | 145 ↔ 130 | 150 ↔ 135 | 155 ↔ 140 | 160 ↔ 144 | 165 ↔ 149 | 170 ↔ 153 | 175 ↔ 158 | 180 ↔ 162 | 185 ↔ 167 | 190 ↔ 171 | 195 ↔ 176 | 200 ↔ 180 |
| Zone 3 | Yellow | 90% ↔ 80% | 108 ↔ 96 | 113 ↔ 100 | 117 ↔ 104 | 122 ↔ 108 | 126 ↔ 112 | 130 ↔ 116 | 135 ↔ 120 | 140 ↔ 124 | 144 ↔ 128 | 149 ↔ 132 | 153 ↔ 136 | 158 ↔ 140 | 162 ↔ 144 | 167 ↔ 148 | 171 ↔ 152 | 176 ↔ 156 | 180 ↔ 160 |
| Zone 2 | Green | 80% ↔ 70% | 96 ↔ 84 | 100 ↔ 88 | 104 ↔ 91 | 108 ↔ 95 | 112 ↔ 98 | 116 ↔ 102 | 120 ↔ 105 | 124 ↔ 109 | 128 ↔ 112 | 132 ↔ 115 | 136 ↔ 119 | 140 ↔ 123 | 144 ↔ 126 | 148 ↔ 130 | 152 ↔ 133 | 156 ↔ 137 | 160 ↔ 140 |
| Zone 1 | Blue | 70% ↔ 60% | 84 ↔ 72 | 88 ↔ 75 | 91 ↔ 78 | 95 ↔ 81 | 98 ↔ 84 | 102 ↔ 87 | 105 ↔ 90 | 109 ↔ 93 | 112 ↔ 96 | 115 ↔ 99 | 119 ↔ 102 | 123 ↔ 105 | 126 ↔ 108 | 130 ↔ 111 | 133 ↔ 114 | 137 ↔ 117 | 140 ↔ 120 |

*Fig. 1*

| THRESHOLD ZONES | Floor | Ceiling |
|---|---|---|
| Zone 5 c | 165 bpm | ↑165 bpm |
| Zone 5 b | 158 bpm | 165 bpm |
| Zone 5 a | 150 bpm | 158 bpm |
| Threshold | 150 bpm | 150 bpm |
| Zone 4 | 135 bpm | 150 bpm |
| Zone 3 | 120 bpm | 135 bpm |
| Zone 2 | 105 bpm | 120 bpm |
| Zone 1 | 90 bpm | 105 bpm |

*Fig. 3*

THRESHOLD TRAINING SYSTEM

The flowing detailed description is of the best presently contemplated mode of carrying out the invention. This description is not to be taken in a limited sense, but is made merely for the purpose of illustrating the general principles of the invention. The scope of the invention is best defined by the appended claims.

BACKGROUND OF THE INVENTION

Field of the Invention

Heart rate is generally calculated as the number of heart contractions in one minute. At rest, the typical adult heart rate lies between 60 and 90 beats per minute ("bpm"). During physical activity such as exercise, one's heart rate increases. Maximum heart rate ("MHR") is the maximum number of contractions in a given amount of time, generally given in bpm. MHR is generally achieved only during the most strenuous of physical activity, and is often advised to be achieved with caution. Even though MHR is generally inversely related to a person's age, it varies greatly from person to person. The most accurate test of MHR is determined by direct measurement using a heart rate monitor during a cardiac stress test.

The relationship between heart rate and exercise has been known for many years. Heart rate is one of the primary means of monitoring the effect of exercise. While many different means may be used to measure physiological status, such as thermometers, metabolic meters, stress monitors and power meters, heart rate measures a blend of physiological status markers and is used most frequently. Most fitness enthusiasts have goals to improve physiological and mental well being, improve athletic performance, or just have fun. For these goals, changes in heart rate may be used to track improvements and to improve the quality and benefits of exercise.

Recently, the health industry has experienced the development of cheaper and more fully featured heart rate monitors. As of this writing, heart rate monitors that would have cost hundreds of dollars just a few years ago are becoming easily attainable for casual athletes looking to attain everyday fitness goals. There are many types of heart rate monitors currently on the market. One popular type comprises a receiver that uses a chest sensor to detect the electrical activity of the heart. The sensors on the chest strap generally comprise electrodes and are placed against the wearer's skin, thereby sensing the electrical fluctuations of the heart. A signal is sent from the chest strap to the receiver, which is typically worn on the wearer's wrist. Heart rate monitors allow detailed and reliable measurements to be taken continuously at times where it would be difficult for one to record heart rate any other way. Advanced heart rate monitors now include features such as average heart rate over a period of time, calories burned, time in a specific heart rate zone, and the capability to output detailed graphs to a personal computer. Through the use of heart rate monitors, one is provided with detailed information regarding his or her respiratory and cardiovascular system's response over time. The explosion of these devices have led to many different schemes for determining "zones" of heart rate ranges to produce varying effects on the human body.

Another type of heart rate monitor is commonly known as the "contact monitor". This type of heart rate monitoring device is found embedded in cardiovascular equipment such as treadmills, elliptical machines, electronic bicycles, rowing machines, and other equipment. Similar to the portable wrist heart rate monitor, an embedded heart rate monitor uses the user's hand in contact with a plate to allow sensors to measure heart rate, which is then displayed on a screen for the user. Contact heart rate monitors give the same data as other monitors, generally in heartbeats per minute.

The earliest of these methodologies were based on MHR, often times a MHR nonspecific to individual fitness enthusiasts. One conventional and now outdated rule of thumb described a zone that included a range of heart rates between 70% to 85% of one's MHR. It was believed that within this zone one would achieve the best fitness gains. Conventionally, the MHR was determined merely by comparing a person's age with the MHR predetermined for that age—generally found on a chart. Due in large part to marketing measures by companies (e.g. that of Polar Electro Oy) it is still generally assumed by many individuals that, as one gets older, one's MHR drops by a set amount and therefore the intensity of one's target zone should drop accordingly. The drawbacks to this method are that (1) each person's MHR is specific to that person and it may be inaccurate to assume a MHR can be based solely on the person's age, and (2) there are great benefits to be reaped by maintaining a person's heart rate in the zones above and below the zone of 70% to 85% MHR, and (3) the effects of maintaining a person's heart rate in a certain zone are further enhanced by the amount of time spent in the zone.

In 1993 the Applicant developed and released the Heart Zones Training Maximum chart and system, used for finding a training load based on MHR. This system still emphasized the importance of zones calculated from MHR, but did not presume to assign a max heart rate based solely on an individual's age. In this system, a training load value calculated by multiplying the duration of the training time by the training zone in which the training is performed. That is zone 1 has a multiplier of 1, zone 2 has a multiplier of 2, and so on, up to zone 5. Total load is this value multiplied again by the frequency of the training.

One downside to this system was the emphasis on static zones. Because the zones were determined based on MHR, the zones did not vary from sport to sport or dynamically match the fitness of an individual over time. An additional downside to this system is the linearity of the weight of the zones does not take into account the fact that increments in exercise intensity above a certain point tend to have exponential effects on stress in the human body.

In an effort to address this problem, the Karvonen formula was developed. The Karvonen Formula was developed to create a zone that was not static. Although in this system, a max heart rate calculated from age alone was used, the zone was also based on one's resting heart rate, and therefore the range of values given was in a sense personalized. In the Karvonen Formula, the lower end of the training zone is one's heart rate reserve×0.50+resting heart rate and the higher end of the training zone is one's heart rate reserve×0.85+resting heart rate, where heart rate reserve is calculated as resting heart rate subtracted from MHR and where MHR is calculated as one's age subtracted from 220. Drawbacks to this method are that the max heart rate is dependent solely on age, and that there is only one zone in which a person may exercise. That is, heart rates above and beyond the training heart rate zone are not accounted for. Finally, the effects of maintaining one's heart rate in a certain zone for a certain amount of time were unaccounted for.

It is now known that MHR varies tremendously from person to person, even in persons of the same age and the same fitness level. MHR also varies from sport to sport and exercise activity to exercise activity. A person's MHR in one sport or exercise can be as much as 20 bpm lower than that same person's MHR in another sport or exercise. Hence, a person's heart rate as compared to that person's own baseline values for the sport or exercise engaged in provides a much better gauge of cardiorespiratory and cardiovascular activity than a comparison against a static set of values to be used for users regardless of activity. The drawback is that in order to avoid comparison against a static set of values for all users across all activities, a person must determine his or her own MHR for the particular sport or exercise in which the he or she is engaged. Although comparison against a static set of values for all users might be easier for some fitness enthusiasts, the benefits of comparison to one's own base line values are worth the extra effort for most people.

The Suunto Company developed a system commonly referred to as the Training Effect, which details training intensities based on a person's MHR calculated for one sport or exercise. Based on this max heart rate, which must be first calculated by the fitness enthusiast using any number of a variety of methods, zones of <60% max heart rate, 60-70% max heart rate, 70-80% max heart rate, 80-90% max heart rate and 90-100% max heart rate have been developed. The lowest level is described as having mostly restorative benefits and being capable of producing benefits in basic fitness, especially after a long break from exercise. The Training Effect methodology continues on to state that the majority of cardiovascular training should occur within the 60-70% zone, that exercising in the 70-80% zone will improve one's agility and efficiency in movement, and warns against overtraining in the 80-90% zone. As the intensity in each zone increases, the Training Effect method also describes the body's inability to process built up lactic acid. At the highest training levels, lactic acid tends to build up in the body much faster than it can be removed, causing discomfort and the need to slow down. While the Training Effect method does disclose the defining of personalized base line levels on which to base target zones, it does not take into account periodization, using anything other than MHR as a basis, or long-term training plans.

There is thus a need for a comprehensive and personalized system for monitoring the effects of training and activity in dynamic zones taking into account the fact that increments in exercise intensity above a certain point tend to have exponential effects on stress in the human body.

SUMMARY OF THE INVENTION

In accordance with the present invention, a training system for aiding the athletic performance and training of health and fitness enthusiasts is provided. The Applicant's system includes a personalized set of intensity zones corresponding to increasing levels of exercise intensity. The personalization of the system is accomplished through determining a threshold level based on oxygen consumption or a numerical rating of perception of effort or lactate or metabolism that is unique to each individual. From this determination, an anchor point is created upon which the heart rate values for each of eight zones are based. Each zone corresponds to a multiplier that when factored in to the amount time spent in each zone by the individual, yields a total training load value.

BRIEF DESCRIPTION OF THE DRAWINGS

The foregoing aspects and many of the attendant advantages of the invention will become more readily appreciated as the same becomes better understood by reference to the following detailed description, when taken in conjunction with the accompanying drawings, wherein:

FIG. 1 depicts a chart in accordance with the present invention, showing a series of zones and an associated range of heart rates in beats per minute.

FIG. 3 depicts a chart in accordance with the present invention, showing the floor and ceiling heart rates for an individual having an anchor point of 150 bpm.

DETAILED DESCRIPTION OF THE INVENTION

Figure 2:
FIG. 2 depicts a chart in accordance with the present invention, showing a simplified model of the zones in FIG. 1, compiled into zone groupings.

The first step of the Applicant's system required the acquisition of heart rate data. Although heart rate is a function of time and can be described according to any time frame, in a preferred embodiment of the invention the individual's rate in beats per minute (bpm) is used.

Second, an anchor point is determined. Conventional systems have traditionally used an individual's MHR as the anchor and upon which all zones were dependent. The Applicant's system utilizes an anchor point based preferably on a threshold level or threshold rate, as defined below. For purposes of this application, threshold level, threshold point, threshold rate, cross-over point, lactate threshold, ventilatory threshold and anchor point are all one and the same in definition.

The threshold rate is the heart rate corresponding to that intensity of exercise corresponding to the dividing point between aerobic and nonaerobic metabolism, as further described below. First, it is noted that $VO_2$ max is the maximum amount of oxygen an individual's body is capable of using in one minute. Traditionally, the value is recorded in milliliters of oxygen per kilogram of weight per minute. More fit individuals tend to have higher $VO_2$ max values, and in general, one's threshold heart rate will increase with increased fitness. The threshold rate is the point at which further increases in exercise intensity will cause the body's metabolism to no longer be aerobic. There are a number of metabolic markers that when measured indicate this changeover point from aerobic to nonaerobic, including but not limited to lactic acid level, oxygen exchange, and carbon dioxide exchange.

One's body can cross over to nonaerobic metabolism (sometimes referred to as anaerobic threshold) because the individual is incapable of using any additional oxygen per unit time. Beyond the threshold point, carbohydrates are processed without the use of oxygen, ultimately leading to the build up of lactic acid in the individual's body. At this point and above, the energy needed by the body to maintain the given intensity level exceeds the oxidative process capabilities of the body, and nonaerobic metabolism begins. Since lactate is a salt substance produced from lactic acid, which itself is a product of muscle contraction, measurement of an individual's lactate level indicates the point at which one's metabolism crosses over from aerobic to nonaerobic. The heart rate of the individual at this dividing point between aerobic and nonaerobic metabolism is the threshold rate.

The threshold rate is sport and exercise specific and dynamic, that is, it changes with an individual's fitness level, nutritional intake, and environmental factors, such as temperature, humidity or altitude. It does not necessarily change with an individuals age. It may be one heart rate for a first exercise (or sport) and a second heart rate for a second exercise (or sport), and for purposes of this application must be determined for the same sport or exercise for which the other of applicant's steps will be used.

The Applicant has found the threshold rate to be one of the strongest predictors of athletic performance, and thus it serves as the anchor point for the Applicant's system.

There are myriad methods for estimating the threshold rate. One of the most accurate and popular methods is the lab testing of blood lactate levels. A typical blood lactate level is 2 millimoles per liter, and anaerobic threshold is commonly held to have occurred when lactic acid concentration reaches 4 millimoles or greater per liter. A second means for lab testing an individuals threshold heart rate number is through testing the ventilatory threshold. Ventilatory threshold is the point at which a person's body metabolism changes from aerobic to nonaerobic. In field-testing it is estimated by a shift in breathing patterns while in lab testing it can be determined by the ratio of carbon dioxide expired and oxygen inspired.

The Applicant's preferred system for estimating the threshold rate is the commonly known as the Talk Test. The Talk Test was first devised by Carl Foster, Ph.D. a professor at the at the University of Wisconsin. In short, the Talk Test suggests the point at which the exercise intensity of an individual is sufficient so that the individuals can no longer comfortably recite aloud a standard paragraph (commonly the Pledge of Allegiance) at a reasonable rate without pausing for breath. This point is the ventilatory threshold point. See Rachel Persinger, Carl Foster, Mark Gibson, Dennis C. W. Fater, John P. Porcari, *Consistency of the Talk Test for Exercise Prescription*, Medicine & Science in Sports & Medicine, March 2004: 1632-1636.

At this crossover intensity level, the ventilatory demands are greater than the ability of the oxygen delivery system to keep up. At this point ventilation rate increases dramatically.

The Applicant provides a brief description of the typical ventilatory status an individual would experience in each of the Applicant's zones:

TABLE 1

Typical user ventilatory status corresponding to zones

| Zone 1 | easy and effortless to breathe |
| Zone 2 | breathing is comfortable and easy |
| Zone 3 | can talk without interruption or difficulty |
| Zone 4 | more difficult to talk, becoming uncomfortable |
| Threshold Zone | Not sure if speaking is comfortable, on the verge of not being able to talk |
| Zone 5a | Challenging, deep and rapid breathing, don't want to talk unless have to |
| Zone 5b | very, very rapid breathing, very uncomfortable, don't want to talk even if forced |
| Zone 5c | cannot talk, ready to stop |

Third, the heart rate values corresponding to the Applicant's zones 1-5c in which one exercises is determined. FIG. 1 shows a detailed schematic of the eight zones present in the threshold training system. Turning now from Table 1 to FIG. 1, the zones are again shown as 1, 2, 3, 4, threshold 5a, 5b, and 5c. The zone is determined as a percentage of the threshold heart rate number, the determination of which was outlined above in step 1. The threshold rate number is located on the chart in the "Anchor Point" row. The column of numbers above and below the person's anchor point should be noted and written down in a separate chart such as that shown in FIG. 3.

Using any of the above methods to determine the anchor point, the data is then matched to a chart as shown in FIG. 1.

Turning now to FIG. 1, attention is brought to the "Threshold" row, which comprises a list of numbers in increments of 5 beats per minute. The closest number corresponding to the anchor point is noted, and then numbers in the column in which the anchor point number resides are also noted. Since a heart rate at the anchor point is 100% of the anchor point value, the corresponding percentage as shown on FIG. 1 is 100%. The other numbers in any given column correspond to a value of the anchor point in that column equal to the value shown for that row in the percentage column.

The zones are determined according to various benefits an individual receives while staying in the zone. AS shown in FIG. 1, the floor and ceiling of each zone in a preferred embodiment are derived from the individual's threshold rate. Although either max heart rate or threshold rate may be utilized in determining these values, the preferred embodiment of the invention uses the threshold rate as the anchor. Increments of 10% of max heart rate or threshold rate are shown on FIG. 1, with the 10% above 100% being further broken down into three zones. Except for Zone 5c, for which there is no zone higher, the upper end of one zone represents the same heart rate percentage as the lower end of the zone above it. For instance, the top of zone 3 and the bottom of zone 4 are both equal to 90% of an individual's threshold rate in the threshold rate system.

As an example case, an individual's threshold rate for one particular activity or exercise was determined to be 148 bpm. In this case, the row "Threshold" would be examined until the number closest to 148 is identified. In this case, 150 is the closest number. The column of numbers corresponding to a threshold rate of 150 is now analyzed. For ease of use, the individual may copy the data from the column to a new chart, as shown in FIG. 3. Note, the bpm values in FIG. 3 correspond to the values in FIG. 1 from the column corresponding to the individual's threshold rate. The heart rate range values also correspond only necessarily correspond to the exercise or activity originally used in the threshold heart rate determining step above.

The Applicant's system further uses the principle of weighted zones, that is, each of the zones has associated with it a multiplier. Higher zones demand more from the body and hence have associated with them a higher multiplier. The multiplier used in the Applicant's system reflects the fact that increments in exercise intensity above a certain point tend to have exponential effects on stress in the human body. The Applicant has found this to be the case through lactate profile measurements taken on humans at varying levels of exercise intensity. Heart rate response above a certain point, defined by the Applicant as the "threshold point," increases exponentially. Up until that point, i.e. from all zones leading up to the threshold zone, the multiplier increases substantially linearly.

Figure 4:
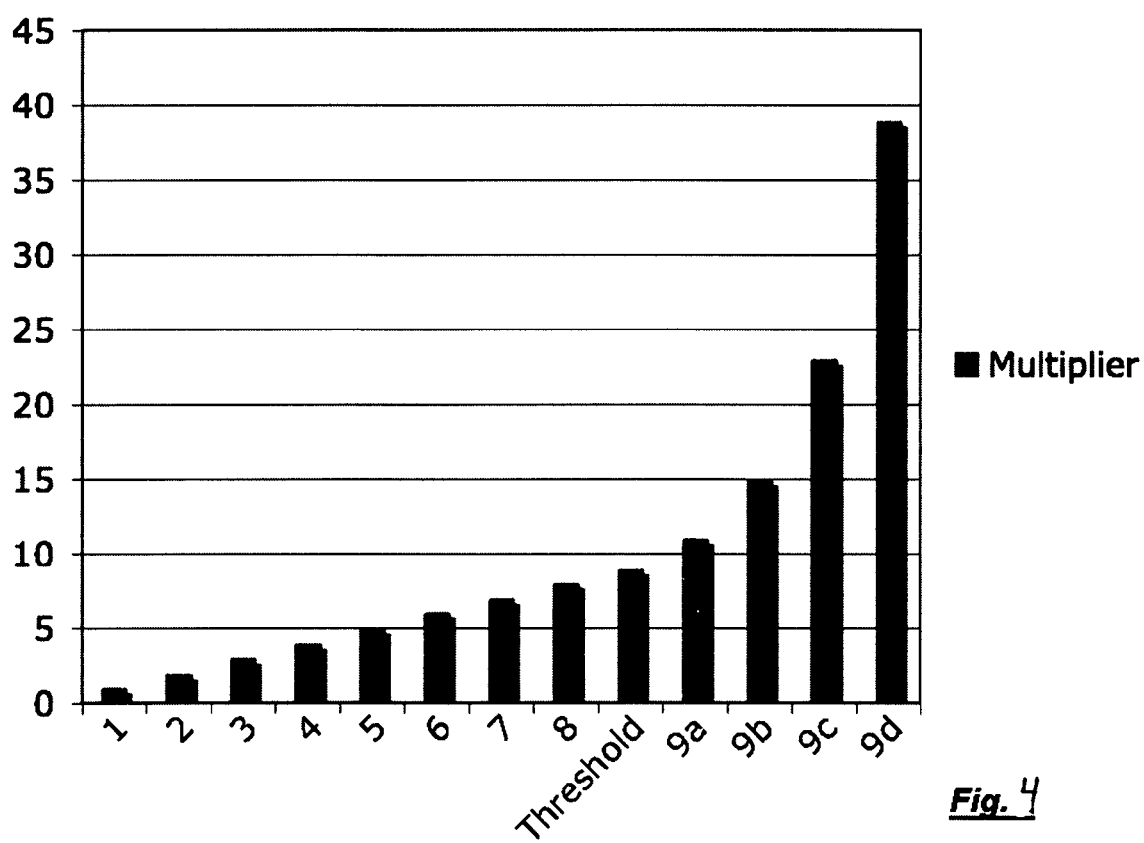
FIG. 4 depicts a chart showing a multiplier associated with a plurality of zones, wherein for the zones preceding a threshold zone a substantially linear increase in multiplier is depicted and wherein for the zones following a threshold zone a substantially exponential increase in multiplier is depicted.

Following the general guidelines from FIG. 4 regarding the range of multipliers falling into the applicant's definition of "substantially exponentially", the Table 2 was produced. This table is one example of the application of a multiplier and as shown throughout this application various multipliers that increase substantially exponentially beyond a threshold point.

TABLE 2

Threshold Training System Zones and multipliers

| Zone Number: | 1 | 2 | 3 | 4 | Threshold | 5a | 5b | 5c |
|---|---|---|---|---|---|---|---|---|
| Zone Weight or Points | 1 | 2 | 3 | 4 | 5 | 6 | 8 | 12 |

It is again important to note that the multiplier value associated with zones 5a-5c in Table two could easily be replaced with the values 60, 80 and 120 and the critical information regarding the total training load (see below) would still be readily apparent to the user.

It is also important to note that the number of zones leading up to the Threshold zone need not necessarily be four. For instance, in an alternative embodiment of the invention, the applicant has eight zones before the threshold zone is reached. See FIG. 4. In this alternative embodiment, the eight zones prior to the threshold zone have, respectively, the multipliers 1, 2, 3, 4, 5, 6, 7, and 8. In this embodiment, the threshold zone multiplier is 9, and the three zones beyond the threshold zone (in this case zones 9a, 9b, 9c and 9d) are, respectively, 11, 15, 23, and 39. The values along the Y-axis are unitless because the important feature is the substantially exponential growth curve in all zones beyond the threshold zone and the substantially linear growth rate in all zones leading up to the threshold zone.

An adjusted value calculated by multiplying the time spent in a zone by the value associated with the zone is then used in the next step of the Applicant's system.

Referring again to FIG. 1, the various zones within the chart are each of a different color that is in accord with the level of intensity of the zone. Zone 1 is the bottom most row and is disclosed as sky blue in color. Zone 2, just above it, is grass green, representing along with zone 1 an easy relaxing zone in which to exercise. Zone 3 is yellow in color, a warning to the user because from this point up intensity is beginning to increase dramatically. Zone 4 is orange and the subparts of Zone 5 are varying shades of red, indicating the highest intensity level. At these highest zones an individual's body cannot process oxygen at a level to keep up with the body's demand, and lactate begins to build up. The Threshold zone in a preferred embodiment is an attention-getting color, such as bright orange-red, white or black.

Different health and fitness benefits are associated with each zone. The benefits an individual receives while in a higher zone are not necessarily duplicated when one is in a lower intensity zone, and vice versa. That is, one does not get the same benefits from zone 1 that one would get training in zone 4. In the high threshold zones, the result of a person's exercise is the building up of tolerance to high acidosis resulting from high lactate production and removal. In the lower threshold zones one is exercising to increase the capillary density and mitochondrial density in the muscle cells. Zone 3 is also referred to as the aerobic zone because at this point the user is beginning to realize large cardiovascular aerobic benefits.

Turning now to FIG. 2, the eight zones are shown condensed into five. For purposes of simplicity, the three zones, 5a, 5b, and 5c, making up zone five as shown in FIG. 1 are now grouped together into one zone 5. Zones 1-3 are referred to collectively as the health zones, because when exercising in this zone the user primarily achieves health benefits such as better sleep at night, increased energy levels, decreased blood pressure levels, improved cholesterol levels and improved response to stress. Zones 2-4 are referred to collectively as the fitness zones, because when exercising in this zone the user primarily achieves fitness benefits such as lower fat levels, healthier metabolism, increased endurance, and increased ability to process oxygen. Zones 3-5 are collectively referred to as the performance benefits because of the performance benefits achieved through exercising within this zone. Performance benefits may include such benefits as increased top speed, increased tolerance to lactic acid buildup, increased ability to sustain high levels of oxygen consumption, and increased $VO_2$ max.

As there is obviously a great deal of overlap within and among the collective groupings of the zones, the grouping is merely a convenience measure for the user, to remind the user quickly that for instance in general, a workout that varies between zones 2, 3, and 4 will primarily be achieving fitness goals while for instance a workout that varies between zones 1, 2, and 3 will primarily be achieving health benefits.

The fourth step of the Applicant's program involves the concept of "training load". Training load is calculated by multiplying the amount of time an individual spends in a particular training zone by the multiplier associated with that training time. If the individual spends the same amount of time in the same training zone 4 times in a week, the value calculated above may again be multiplied by four to obtain the training load for the week.

Training load is an important concept because it allows an individual to track his or her training performance over time. By assigning multipliers that increase substantially exponentially with each zone from the threshold zone and above, the physiological effects of higher intensity activities is properly accounted for.

In short, training load may be calculated as intensity (as determined by the Applicant's multipliers)×frequency×time. Additional factors could readily be added such as an additional activity-specific multiplier to standardize the training load value between different activities. For instance, the training load value obtained could be multiplied by 1.2 if the activity was swimming and by 0.8 if the activity was cycling.

For purposes of demonstration, multipliers of 1, 2, 3, 4, 5, 6, 8, and 11 were selected; conforming to the Applicant's method is shown in Table 3, below. Here, 240 minutes in zone three under yields a total training load for that session of 720. The total training load is 1680. Multiplying this by 10 weeks at a frequency of 1 time per week would yield a training load for the ten weeks of 16800.

TABLE 3

| Calculating Training Load in the threshold training system | | | | | | | | | |
|---|---|---|---|---|---|---|---|---|---|
| Preparation 1 | Endurance Base | 20% | 30% | 40% | 20% | — | — | — | — |
| TIME IN ZONE | 10 hours × 60 min = 600 weekly minutes x | 120 min. | 180 min | 240 min | 120 min | — | — | — | — |
| POINTS | Heart Zones Training Point (Zone weight) multiplier | 1 | 2 | 3 | 4 | 5 | 6 | 8 | 11 |
| LOAD | Internal Training Load | 120 | 360 | 720 | 480 | | | | |

The following table was generated using a set of multiplier values following the same substantially exponential increase as defined above and shown in Table 3, but with different values associated with the multipliers.

TABLE 4

| Calculating Training Load in the threshold training system | | | | | | | | | |
|---|---|---|---|---|---|---|---|---|---|
| Preparation 1 | Endurance Base | 20% | 30% | 40% | 20% | — | — | — | — |
| TIME IN ZONE | 10 hours × 60 min = 600 weekly minutes x | 120 min. | 180 min | 240 min | 120 min | — | — | — | — |
| POINTS | Heart Zones Training Point (Zone weight) multiplier | 3 | 6 | 9 | 12 | 15 | 19 | 25 | 35 |
| LOAD | Internal Training Load | 120 | 360 | 720 | 480 | | | | |

If necessary, from this training load determination step, periodization as known in the art may be performed. Periodization is essentially a training load value distributed over many weeks, months, or years. Continuing the discussion with periodization: Periodization refers to the distribution and sequencing of training load, as shown above. To distribute workload over weeks or months of training and to sequence it with appropriate weighting and unweighting the training needs to be quantifiable. Only recently has this quantification become possible, through the use of new tools like heart rate monitors, distance monitors, altitude monitors, and speed monitors. With these types of tools it has recently become possible for amateur exercise enthusiasts to easily assess the amount of stress and load that one is experiencing.

The Applicant has found through experimentation that fitness levels increase optimally when an individual spends time within each different heart zone. Sports periodization plans, such as those dating back to Selye's General adaptation system from the late 1950s, may be adapted to include the threshold zones and associated multipliers disclosed by the applicant.

Periodization plans may be personalized, should be variable (to prevent training monotony and to stimulate positive effects from training), should be planned according to the amount of time an individual expects to have for training, and should be logged. Accurate logging is critical in gauging the effectiveness of a training program. In particular, details about the training and about the context of one's life in which the training occurs should be logged. Recovery or regeneration time should also be built into any periodization plan.

In use, a fitness enthusiast using the Applicant's training system should not measure or gauge his or her workout based on the number of beats per minute at which she is training. Instead, the user should think of training as a certain percentage of the threshold anchor point, or, in an alternative embodiment of the invention, as a certain percentage of the MHR.

The steps outlined above, i.e. determining anchor point using a means such as the Talk Threshold test, and referring to the chart shown in FIG. 1 to determine an anchor point and upper and lower limits of each zone, defines information referred to as the user's personalized zone fitness information.

Once the user of the Applicant's system has determined his or her own personalized zone fitness information; it is ideally printed in the form of a chart that may be easily accessible during the user's physical activity. FIG. 3 depicts a sample chart created using threshold system. Note that except for the highest zone, the ceiling of one zone corresponds to the floor of the zone above it.

In an alternative embodiment of the present invention the multiplier growth curve shown in FIG. 4 rises substantially exponentially with from the first zone to the last zone. That is, rather than a linear increase in multiplier from one zone to the next leading up to the threshold zone, this alternative embodiment of the invention utilizes a substantially exponential growth curve for the multiplier across the entire chart, without regard for the threshold zone.

In an additional alternative embodiment of the present application, multiplier values are stored in a computer-readable medium for display on a device such as a personal computer, mobile telephone (including telephone/PDA devices), or web application. The display system on said devices in this alternative embodiment would display information regarding the threshold rate and associated zones for an individual. For instance, Table 3 and FIG. 3 above are suitable examples for this display. The computer-readable medium further stores instructions to determine a personalized heart rate range for each of said zones, wherein the range is a percentage of the anchor point heart rate. The means for determining training load as described above could without difficulty be implemented by a computer program.

With respect to the above description then, it is to be realized that the disclosed equations, figures and charts may be modified in certain ways while still producing the same result claimed by the Applicant. Such variations are deemed readily apparent and obvious to one skilled in the art, and all equivalent relationships to those illustrated in the drawings and equations and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact disclosure shown and described, and accordingly, all suitable modifications and equivalents may be resorted to, falling within the scope of the invention.

I claim:

1. A method for creating on a chart a personalized set of intensity zones of an individual, the method comprising:
   a. measuring blood lactate level of an individual while the individual exercises, and calculating therefrom a threshold heart rate corresponding to a lactic acid metabolic marker;
   b. determining an anchor point based on said threshold heart rate;
   c. providing:
      i. a computer readable memory for storage of said anchor point; and
      ii. a processor in communication with said memory that contains instructions that determine a heart rate range as a percentage of said anchor point for each of a plurality of heart rate intensity zones, wherein said heart rate range comprises an upper heart rate and a lower heart rate, and wherein one of said intensity zones comprises a threshold zone beyond which zones of higher intensity correspond to increases in said metabolic marker;
   d. determining a multiplier associated with each said intensity zone; and e. printing a chart comprising personalized information regarding said intensity zones and said anchor point.

2. The of method claim 1 wherein said chart comprises major subdivisions that correspond to said intensity zones, and one of said major subdivisions is further divided into a plurality of minor subdivisions.

3. The method of claim 2 wherein each of said major subdivisions corresponds to a color.

4. The method of claim 1 wherein said individual's heart rate is within said heart rate range for an amount of time, said system further comprising the step of multiplying said amount of time by said multiplier to determine a training load.

5. The method of 1 wherein for intensity zones above said threshold zone said multiplier is substantially exponentially related thereto.

6. The method of claim 5 wherein intensity zones below said threshold zone have a substantially linear correspondence to said multiplier.

7. The method of claim 1 wherein metabolic markers relate to lactic acid level or oxygen exchange rates.

8. A method of creating on a chart a personalized set of intensity zones for an individual, the method comprising the steps of:
   a. determining a threshold heart rate of an individual as the individual partakes in an activity, wherein said threshold heart rate is determined by measuring a blood lactate level of the individual and determining a corresponding lactic acid metabolic marker;
   b. determining an anchor point based on said threshold heart rate;
   c. providing:
      i. a computer readable memory for storage of said anchor point; and
      ii. providing a processor in communication with said memory and that contains instructions that generate based on said anchor point a personalized heart rate range for each of a plurality of heart rate intensity zones including one threshold zone beyond intensity zones correspond to an increase in lactic acid buildup, and wherein each said intensity zone corresponds to a multiplier; and
   d. printing a chart comprising said personalized heart rate range and said anchor point.

9. The method of 8 wherein said intensity zones are readable in chart or graph form, and wherein said chart comprises major subdivisions that correspond to said intensity zones, and one of said major subdivisions is further divided into a plurality of minor subdivisions.

10. The method of 9 wherein each of said major subdivisions corresponds to a color.

11. The method of 8 further comprising applying said heart rate range to the activity in said determining a threshold heart rate step.

12. The method of 8 wherein a heart rate of said individual is within said heart rate range for an amount of time, further comprising the step of multiplying said amount of time by said multiplier to determine a training load.

13. The method of 8 wherein said intensity zones are associated with metabolic markers comprising oxygen and lactate.

14. The method of 8 wherein for increases in intensity zones beyond said threshold zone said multiplier association is substantially exponential.

15. The method of 14 wherein for increases in intensity zones below said threshold zone said multiplier association is substantially linear.

\* \* \* \* \*